(12) United States Patent
Davidian

(10) Patent No.: US 6,595,970 B1
(45) Date of Patent: Jul. 22, 2003

(54) OPHTHALMIC DEVICE FOR DISPENSING EYEDROPS

(76) Inventor: James L. Davidian, 6800 Rolling Hills, Riverside, CA (US) 92505

( * ) Notice: Subject to any disclaimer, the term of this patent is extended or adjusted under 35 U.S.C. 154(b) by 0 days.

(21) Appl. No.: 09/994,310

(22) Filed: Nov. 26, 2001

(51) Int. Cl.[7] .............................................. A61M 37/00
(52) U.S. Cl. ........................ 604/300; 604/302; 604/298
(58) Field of Search ................................ 604/292–302, 604/289

(56) References Cited

U.S. PATENT DOCUMENTS

| | | | |
|---|---|---|---|
| 2,382,771 A | 8/1945 | Bowers | 128/233 |
| 2,676,592 A | 4/1954 | Wood | 128/233 |
| 3,058,466 A | 10/1962 | Routsong | 128/233 |
| 3,521,636 A | 7/1970 | Mahoney et al. | 128/233 |
| 3,934,590 A | 1/1976 | Campagna et al. | 128/233 |
| 4,131,115 A | 12/1978 | Peng | 128/249 |
| 4,134,403 A | 1/1979 | Johnsen et al. | 128/233 |
| 4,344,430 A | 8/1982 | Astrove | 128/233 |
| 4,531,944 A | 7/1985 | Bechtle | 604/302 |
| 4,543,096 A | 9/1985 | Keene | 604/300 |
| 4,792,334 A | 12/1988 | Py | 604/301 |
| 4,946,452 A | 8/1990 | Py | 604/301 |
| 5,059,188 A | 10/1991 | Goddard | 604/300 |
| 5,267,986 A | 12/1993 | Py | 604/294 |
| 5,578,020 A | 11/1996 | Mosley | 604/295 |
| 5,713,495 A | 2/1998 | Menard | 222/212 |
| 5,810,794 A | 9/1998 | Peplinski | 604/295 |
| 6,371,945 B1 * | 4/2002 | Sherman | 604/300 |

\* cited by examiner

Primary Examiner—Weilun Lo
Assistant Examiner—Linh Truong
(74) Attorney, Agent, or Firm—F. Eugene Logan

(57) ABSTRACT

An ophthalmic device for dispensing of an eyedrop from a resilient eyedrop dispenser. The ophthalmic device has an upper body portion having a front portion, first and second lever arm members rigidly connected to the front portion and extending in a longitudinal direction therefrom with distal ends of the arm members being spaced apart. An opening in the upper body portion for receiving the eyedrop container with outlet pointing down. Squeezing the arm members together reduces the opening thereby dispensing an eyedrop. An alignment projection is attached to the upper body portion and has a lower distal end for resting on an user facial area, thereby facilitating maintaining the outlet of the eyedropper container in alignment with a recipient eye. Sighting apertures are also provide to further insure proper alignment over the eye. The ophthalmic device has a shape effective for producing by injection molding.

25 Claims, 4 Drawing Sheets

OPHTHALMIC DEVICE FOR DISPENSING EYEDROPS

BACKGROUND OF THE INVENTION

Devices for applying eye medication solutions to the eye have ranged from the simple eyedropper to soft-sided squeezable plastic eyedrop containers having an integral dropper outlet to fairly complex soft-sided squeezable plastic eyedrop container designs to devices with many assembled parts. The soft-sided squeezable plastic eyedrop containers range from the most popular cylindrical and rectangular cross-sectional containers to more complex designs which currently appear to have attracted little, if any, commercial interest. A review of U.S. patents revealed the following designs.

U.S. Pat. No. 5,810,794 is directed towards a device, which rests on the facial area around the eye, for use with a conventional eyedropper bottle. The eyedropper bottle is surrounded by a pair of loosely hinged pincer wings which when squeezed squeeze the eyedropper bottle.

U.S. Pat. No. 5,713,495 is directed towards a simple device which hold the neck of a conventional eyedropper bottle. The device is held by one hand while the other hand squeezes the eyedropper bottle directly.

U.S. Pat. No. 5,578,020 discloses a device having a long eyedropper tube which is connected to an eyedropper bottle. The dropper tube is surrounded by a dispensing sleeve made of elastomeric material which rests on the facial area around the eye. The user squeezes the device which squeezes the eyedropper tube which releases the eyedrops.

U.S. Pat. No. 5,267,986 discloses a complex device having a piston-like or accordion-like dispenser-vial, a trigger and a projecting finger for engaging the lower eye lid. When the trigger is depressed, a drop of medicament is released.

U.S. Pat. Nos. 5,154,711 and 5,059,188 are directed towards devices with sighting apertures which hold the neck of an eyedropper bottle and rest on the user's forehead and/or nose. The eyedropper bottle is squeezed directly by the user to release eyedrops.

U.S. Pat. Nos. 4,946,452 and 4,792,334 and 4,543,096 are directed towards various devices which hold eyedropper bottles and push the user's eyelids apart simultaneously as the device is squeezed to release the eyedrops.

U.S. Pat. No. 4,531,944 discloses a facially contoured device for resting on the facial area surrounding the eye socket, and for holding an eyedropper or eyedropper container. The device has a sighting aperture. The eyedropper or eyedropper container is squeezed directly by the user to release eyedrops.

U.S. Pat. No. 4,344,430 is directed towards a mirrored sighting device for holding an eyedropper or eyedropper bottle. The eyedropper or eyedropper bottle is squeezed directly by the user to release the eyedrops.

U.S. Pat. No. 4,134,403 is directed towards a simple device which holds an eyedropper bottle and rests on the user's nose. The eyedropper bottle is squeezed directly by the user to release eyedrops.

U.S. Pat. No. 3,934,590 discloses a simple tripod-like device for holding the outlet-neck portion of an eyedropper bottle. The device rests on the user's nose, cheekbone and brow. The eyedropper bottle is squeezed directly by the user to release eyedrops.

U.S. Pat. No. 3,521,636 is directed towards a specially designed eyedropper bottle having an offset projection for resting on the user's nose. The eyedropper bottle is squeezed directly by the user to release eyedrops.

U.S. Pat. No. 3,058,466 discloses a simple device which holds the neck of an eyedropper bottle and rests on the user's cheekbone and brow. The eyedropper bottle is squeezed directly by the user to release eyedrops.

U.S. Pat. No. 2,676,592 is directed towards a device for holding the outlet end of an eyedropper over the eye. While the device is resting on the user's nose, the eyedropper is squeezed directly by the user to release eyedrops.

U.S. Pat. No. 2,382,771 discloses a mirrored sighting device for holding and viewing simultaneously the eye and the eyedropper tip. The eyedropper is squeezed directly by the user to release eyedrops.

U.S. Pat. No. 4,131,115 discloses a complex device, having many parts, for washing the eye while holding back the eyelids. The device contains a squeezable chamber for holding fresh eyewash solution and a collection chamber for collecting the waste or dirty eyewash solution drained from the eye.

SUMMARY OF THE INVENTION

This invention is directed to ophthalmic devices for use with the popular soft-sided squeezable plastic eyedrop containers usually found in all drug stores in the Americas. Such eyedropper containers usually have a round or rectangular cross section.

Self medication of the eye is difficult for many since positioning the eyedropper container close to the eye, while keeping the eye open just as the container is squeezed requires resisting the natural reaction to blink to prevent a foreign substance from entering the eye. For many seniors, coordinating simultaneous positioning and squeezing of the container becomes even more difficult, often resulting in missing the eye and/or over medicating. Therefore, there is a need for an ophthalmic device which holds the eyedropper container, allows easy alignment of the outlet of the eyedropper container over the eye, and requires only a relatively quick and small force to release one eyedrop, or a predetermined small number of eyedrops, per squeeze. This invention is directed to such an ophthalmic device.

In this invention an alignment means which rests on a facial area steadies the device as the device is squeezed between the thumb and the index finger. Usually the right hand is used for the right eye and the left hand is used for the left eye.

In this invention a pair of lever arm members allows the eyedropper container to be easily and quickly squeezed with less force than required to depress the eyedropper container directly by the user's fingers.

In one embodiment of this invention sighting apertures are provided which enable the user to easily determine when the outlet of the eyedropper container is over the eye, either over the sclera, or white of the eye, or if desired over the cornea.

Accordingly, there is provided by the principles of the present invention an ophthalmic device for facilitating dispensing of an eyedrop from a resilient eyedrop container having an eyedrop dispensing outlet. The ophthalmic device comprises an upper body portion having a front portion, a first lever arm member rigidly connected to the front portion and extending in a longitudinal direction therefrom, and a second lever arm member rigidly connected to the front portion and extending in a longitudinal direction therefrom. The distal ends of the first and second lever arm members are spaced apart. An opening is provided in the upper body portion effective for receiving the eyedrop container with the outlet pointing down.

The ophthalmic device provides means effective for reducing the cross-sectional area of the opening when the lever arm members are squeezed together thereby facilitating compressing the eyedrop container when received in the opening sufficiently for causing an eyedrop to be dispensed. The ophthalmic device also includes alignment means attached to the upper body portion. The alignment means has a lower distal end for resting on an user facial area, thereby facilitating maintaining the outlet of the eyedropper container in alignment with a recipient eye while the lever arm members are squeezed together to dispense the eyedrops.

In one embodiment of this invention the upper body portion is unitary in construction. In another embodiment, the entire ophthalmic device is unitary in construction. In still another embodiment, the ophthalmic device has a shape effective for being produced from plastic material by injection molding. In yet another embodiment, the shape of the ophthalmic device is effective for producing from plastic material in a single injection molding step.

In one embodiment of this invention the ophthalmic device is free of hinges, pivots or parts which rotate or pivot or slide with respect to other parts.

In one embodiment of this invention the opening for receiving the eyedropper container is round. In another embodiment, the opening is rectangular. In still another embodiment, the opening is elliptical. Of course, opening 26 may be shaped to fit the cross section of any eyedropper container desired or an adapter provided to convert a round opening 26 to any other shape.

In one embodiment of this invention, the means effective for reducing the opening when the lever arm members are squeezed together includes at least a void space extending in the longitudinal direction between the opening and the lever arm members. In another embodiment, the void space includes eyedrop limitation means effective for preventing dispensing of an over-supply of eyedrops per squeeze of the lever arm members. In still another embodiment, the void space is a narrow slit effective for limiting a maximum number of eyedrops dispersed from the eyedropper container for a single squeeze of the lever arm members to no greater than three. In yet another embodiment, the eyedrop limitation means is effective for facilitating dispensing of but a single eyedrop per squeeze of the lever arm members.

In one embodiment of this invention the means effective for reducing the opening when the lever arm members are squeezed together includes at least one resilient region proximate the opening. In another embodiment, the means effective for reducing the opening when the lever arm members are squeezed together includes at least two diametrically opposing resilient regions proximate the opening.

In one embodiment of this invention the alignment means is attached to the front portion of the upper body portion. In another embodiment, a distal end of the alignment means is concave to enable it to be easily positioned over the bridge of the user's nose.

One embodiment of this invention further comprises container stop means for seating the eyedrop container in the opening and preventing the outlet of the eyedrop container from extending further than a predetermined distance below the opening. In a further embodiment, the container stop means is located on the alignment means. In a still further embodiment, the container stop means is above the lower distal end of the alignment means and extends partly under the opening of the main body means. In yet a further embodiment, the container stop means conforms to a shoulder of the eyedrop container.

In one embodiment of this invention the ophthalmic device further comprises a sighting aperture for facilitating aligning the outlet of the eyedrop container directly over the recipient eye. In another embodiment, the sighting aperture is in the upper body portion. In still another embodiment, there are two diametrically opposed sighting apertures for the right and left eyes.

Referring to FIG. 3,

L=the distance between the center of the opening 26 and the distal ends of lever arm members 23 and 24, and D=the diameter of opening 26.

In one embodiment of this invention the ratio, L/D is at least 1.0. In preferred embodiment the ratio, L/D, is at least about 1.5, and in a most preferred embodiment the ratio, L/D, is at least about 2.

DESCRIPTION OF THE PREFERRED EMBODIMENT

Figure 1:
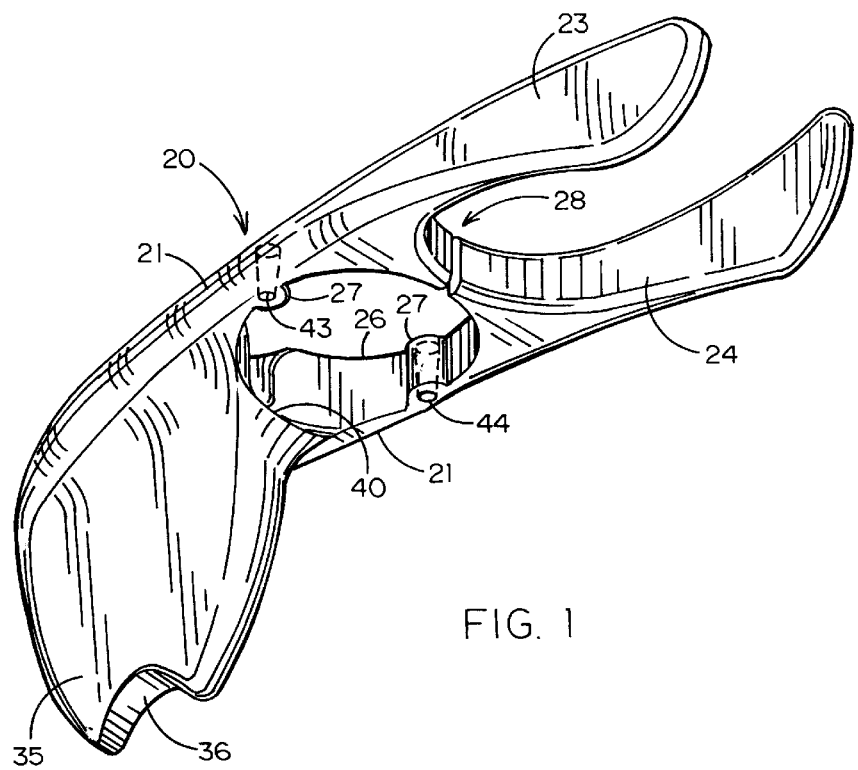
FIG. 1 is bottom, left side perspective view of an ophthalmic device of this invention.
Figure 2:
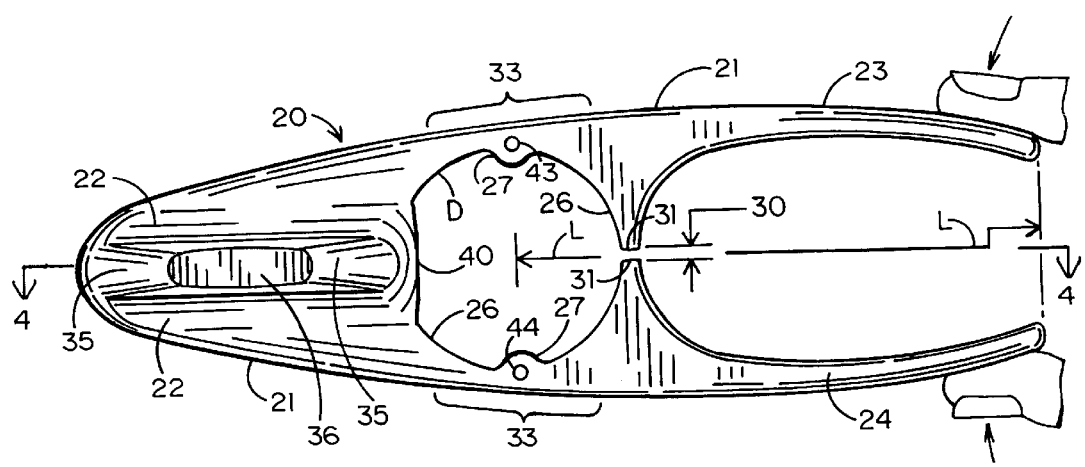
FIG. 2 is a bottom plan view of the ophthalmic device of FIG. 1.
Figure 3:
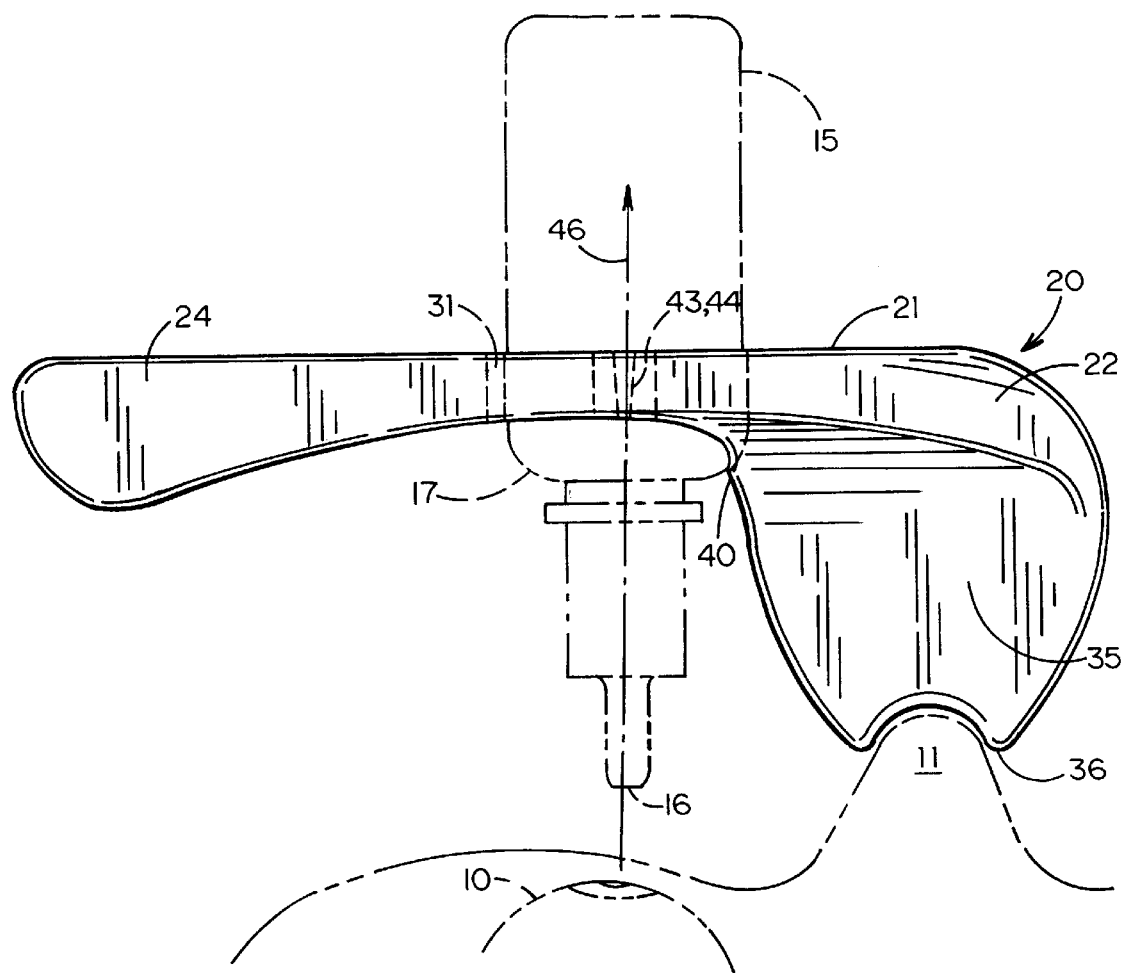
FIG. 3 is a right side elevational view of the ophthalmic device of FIG. 1 holding an eyedropper container shown in phantom, the left side elevational view being the mirror image of FIG. 3.
Figure 4:
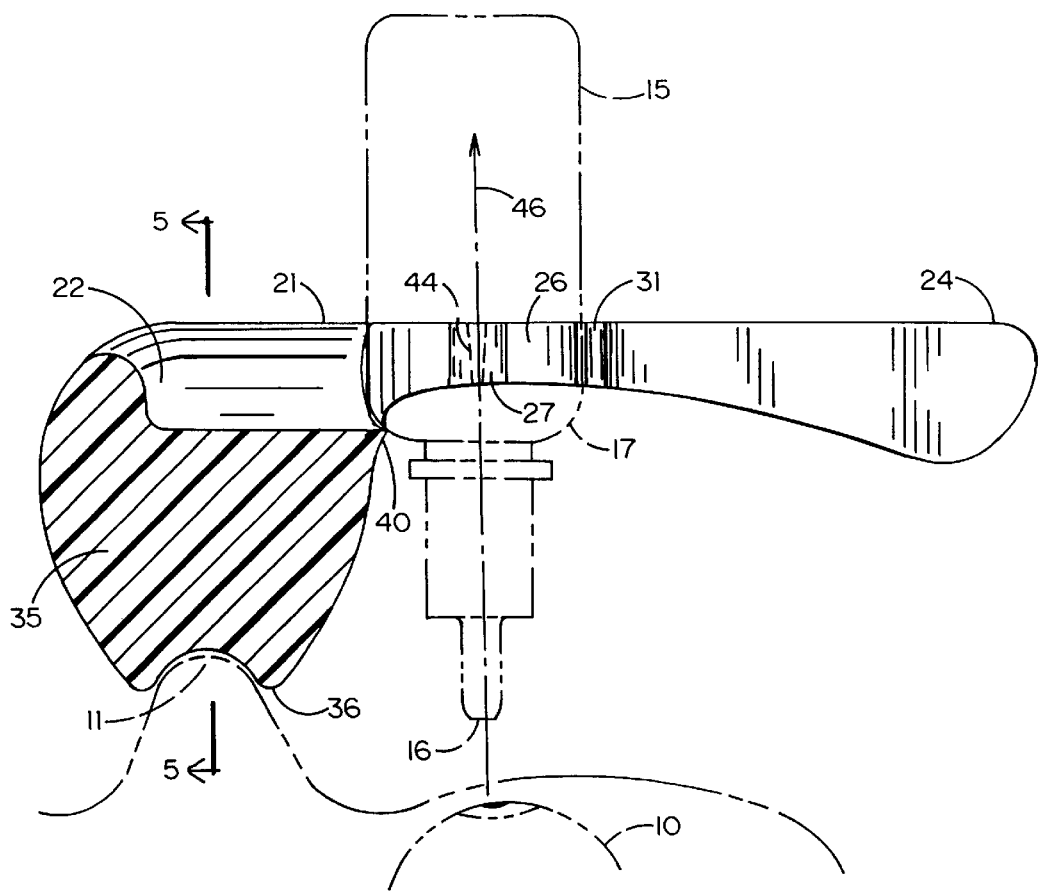
FIG. 4 is a cross-sectional view taken in the direction of line 4—4 of FIG. 2 showing the right half of the ophthalmic device holding the eyedropper container shown in phantom, the left half of the ophthalmic device being the mirror image of FIG. 4.
Figure 5:
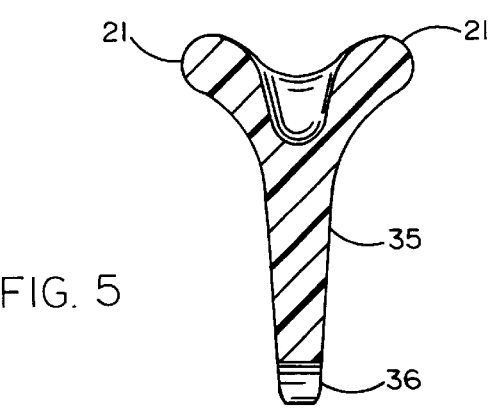
FIG. 5 is a cross-sectional view taken in the direction of line 5—5 of FIG. 4.

FIGS. 1–5 illustrate an ophthalmic device 20 for facilitating the dispensing of liquid or liquid dispersion medications into a recipient eye 10 of the user. In particular, FIGS. 3 and 4 illustrates the ophthalmic device 20 of this invention with a conventional eyedropper container 15 shown in phantom positioned over a recipient eye 10 and supported on a facial area 11 of the user. In FIGS. 1 and 2 eyedropper container 15, facial area 11, and recipient eye 10 are not shown.

Ophthalmic device 20 has an upper body portion 21 having a front portion 22, a first or left lever arm member 23 extending in a longitudinal direction and a second or right lever arm member 24, also extending in a longitudinal direction. Between front portion 22 and lever arm members 23 and 24 there is a predetermined shaped opening 26 for receiving resilient eyedrop container 15 with the outlet 16 directed downward. In this embodiment opening 26 is round and has an inside diameter the same size or slightly larger than the outside diameter of eyedrop container 15 so that the container 15 can be easily inserted into opening 26 with outlet 16 directed downward. Opening 26 can, of course, be shaped to fit the cross section of the particular eyedropper container to be used with the ophthalmic device 20. Preferably opening 26 contains semicylindrical bosses 27 which serve to frictionally retain eyedropper container 15 in opening 26 and facilitate the compression of eyedropper container 15 when lever arm members 23 and 24 are squeezed together.

A void space 28 extends between opening 26 and the most rearwardly extending portions of the lever arm members 23 and 24, respectively. Upper body portion 21 is constructed from a resilient material which provides means effective for reducing opening 26 when the lever arm members 23 and 24 are squeezed together, thereby facilitating compressing container 15 when seated in opening 26 sufficiently for causing an eyedrop to be dispensed.

Void space 28 includes eyedrop limitation means effective for preventing dispensing of an over-supply of eyedrops per squeeze of the lever arm members. Preferably eyedrop limitation means is a narrow slit having a width 30 effective for limiting a maximum number of eyedrops dispersed from the eyedropper container to no greater than three eyedrops per squeeze of the lever arm members, and especially preferably limited to one eyedrop per squeeze. When lever arm members are squeezed together enough to close space 28 between the opposing vertical faces 31 of void space 28, a predetermined number of drops of medication is dispensed from eyedropper container 15.

Non-limiting examples of a resilient material are plastics, woods, laminated woods, and metals with cross sections thin enough to provide an effective amount of resiliency for reducing the size of opening 26 when the lever arm members 23 and 24 are squeezed together. In this embodiment, effective resilient regions 33 exist in upper body portion 21 proximate opening 26 due to the relatively thinner thickness of upper body portion 21 at regions 33.

An alignment means 35 is attached to the bottom of front portion 22 of the upper body portion 21. Alignment means 35 has a lower distal end 36 for resting on a facial area 11 of the user, thereby facilitating maintaining outlet 16 of eyedropper container 15 above the recipient eye 10 while lever arm members 23 and 24 are squeezed together. In the example illustrated in FIGS. 3 and 4, the distal end 36 is concave and the facial area 11 is the bridge of the nose of the user.

Lever arm members 23 and 24 are preferably fixedly attached together thereby forming an unitary construction for upper body portion 21. Furthermore, alignment means 35 is preferably fixedly attached to upper body portion 21 so that the entire ophthalmic device 20 is an unitary construction. Such unitary construction can be performed, for example, by bonding or fusing lever arm members 23 and 24 to front portion 22 to form upper body portion 21, and then bonding upper body portion 21 and alignment means 35 together if the material of construction is wood or other bondable material; or injection molding of the entire ophthalmic device if the material of construction are suitable injection moldable plastics. Such suitable injection moldable plastics are well known in the art. In one embodiment of this invention the entire ophthalmic device is produced in one injection molding operation.

A container stop means 40 is also provided, preferably as part of alignment means 35, which extends partly under opening 26. In the embodiment illustrated in FIGS. 1–5, container stop means 40 engages a shoulder 17 of eyedropper container 15 thereby preventing outlet 16 of eyedrop container 15 from extending further below the opening 26. Container stop means 40 is a predetermined distance below the bottom of opening 26 and a predetermined distance above distal end 36 of alignment means 35 so that outlet 16 can be easily positioned an effective distance above recipient eye 10 with the bridge of the user's nose 11 serving as a resting area for steadying the ophthalmic device 20 as lever arm members 23 and 24 are squeezed together, thereby facilitating alignment of outlet 16 over the eye 10.

To further assist the user in positioning outlet 16 of eyedropper container 15 directly over recipient eye 10, first and second sighting apertures 43 and 44 are also provided in upper body portion 21. In one embodiment, sighting apertures 43 and 44 are conical-shaped having vertically oriented axes which are contained in bosses 27. Such conical-shaped sighting apertures are operable for facilitating release in an injection molding process.

When the ophthalmic device 20 is properly aligned directly over the recipient eye 10 the user can see through one or both of sighting apertures 43 and 44, as indicated by sight lines 46. When the ophthalmic device 20 of this invention is not directly over recipient eye 10 light can not be seen through either of sighting apertures 43 and 44 because of their relatively small size. Either or both of the sighting apertures can be used when medicating each of the user's eyes.

It will be realized that the ophthalmic device of this invention provides considerable mechanical leverage to the eyedropper container. For example with reference to FIG. 3, the ratio L/D is at least about 2.3.

Figure 6:
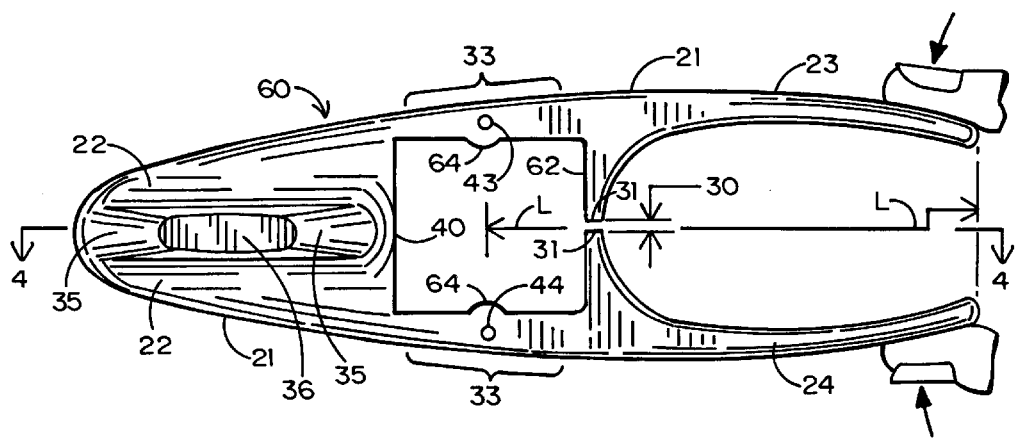
FIG. 6 is a bottom plan view of a second embodiment of an ophthalmic device.

FIG. 6 illustrates a second embodiment 60 of this invention having a square opening 62 with bosses 64 for receiving an eyedropper container having approximately a square cross section.

Figure 7:
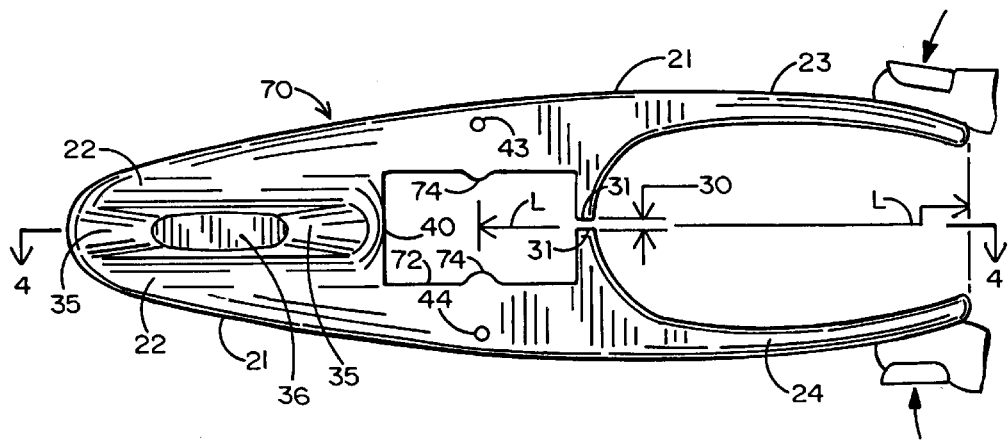
FIG. 7 is a bottom plan view of a third embodiment of an ophthalmic device.

FIG. 7 illustrates a third embodiment 70 of this invention having a rectangular opening 72 with bosses 74 for receiving an eyedropper container having approximately a rectangular cross section. Embodiment 60 and 70 function in the same manner as embodiment 20.

While the preferred embodiments of the present invention have been described, various changes, adaptations and modifications may be made thereto without departing from the spirit of the invention and the scope of the appended claims. The present disclosure and embodiments of this invention described herein are for purposes of illustration and example and modifications and improvements may be made thereto without departing from the spirit of the invention or from the scope of the claims. The claims, therefore, are to be accorded a range of equivalents commensurate in scope with the advances made over the art.

What is claimed is:

1. An ophthalmic device for facilitating dispensing of an eyedrop from a resilient eyedrop container having a drop dispensing outlet, the ophthalmic device comprising:

an upper body portion having a front portion, a first lever arm member rigidly connected to the front portion and extending in a longitudinal direction therefrom, and a second lever arm member rigidly connected to the front portion and extending in the longitudinal direction therefrom, with distal ends of the first and second lever arm members being spaced apart;

an opening in the upper body portion effective for receiving the eyedrop container with the outlet pointing down;

means effective for reducing the opening when the lever arm members are squeezed together thereby facilitating compressing the eyedrop container when received in the opening sufficiently for causing an eyedrop to be dispensed; and alignment means attached to the upper body portion, the alignment means having a lower distal end for resting on an user facial area, thereby facilitating maintaining the outlet of the eyedropper container in alignment with a recipient eye while the lever arm members are squeezed together.

2. The ophthalmic device of claim 1, further comprising container stop means for seating the eyedrop container in the opening and preventing the outlet of the eyedrop container from extending further than a predetermined distance below the opening.

3. The ophthalmic device of claim 1, wherein the means effective for reducing the opening when the lever arm members are squeezed together includes at least a void space extending in the longitudinal direction between the opening and the lever arm members.

4. The ophthalmic device of claim 1, wherein the upper body portion is a single piece in construction.

5. The ophthalmic device of claim 1, wherein the ophthalmic device is a single piece in construction.

6. The ophthalmic device of claim 1, wherein the alignment means is attached to the front portion of the upper body portion.

7. The ophthalmic device of claim 1, wherein the ophthalmic device has a shape effective for producing from a plastic material by injection molding.

8. The ophthalmic device of claim 1, wherein the ophthalmic device has a shape effective for producing from a plastic material by injection molding in a single step.

9. The ophthalmic device of claim 2, wherein the container stop means is above the lower distal end of the alignment means and extends partly under the opening of the main body means.

10. The ophthalmic device of claim 1, further comprising a sighting aperture for facilitating aligning the outlet of the eyedrop container directly over the recipient eye.

11. The ophthalmic device of claim 1, further comprising a sighting aperture in the upper body portion for facilitating aligning the outlet of the eyedrop container directly over the recipient eye.

12. The ophthalmic device of claim 1, further comprising a sighting aperture for facilitating aligning the outlet of the eyedrop container directly over the recipient right eye, and a sighting aperture in the main body means for facilitating aligning the outlet of the eyedrop container directly over the recipient left eye.

13. The ophthalmic device of claim 1, wherein the opening is round.

14. The ophthalmic device of claim 1, wherein the opening is elliptical.

15. The ophthalmic device of claim 1, wherein the opening is rectangular.

16. The ophthalmic device of claim 3, wherein the void space includes drop limitation means effective for preventing dispensing of an over-supply of drops per squeeze of the lever arm members.

17. The ophthalmic device of claim 3, wherein the void space includes drop limitation means effective for facilitating dispensing of but a single drop per squeeze of the lever arm members.

18. The ophthalmic device of claim 3, wherein the void space is a narrow slit effective for limiting a maximum number of drops dispersed from the eyedropper container for a single squeeze of the lever arm members to no greater than three.

19. The ophthalmic device of claim 2, wherein the container stop means conforms to a shoulder of the eyedrop container.

20. The ophthalmic device of claim 1, further comprising: container stop means for seating the eyedrop container in the opening and preventing the outlet of the eyedrop container from extending further than a predetermined distance below the opening; and wherein the ophthalmic device has a shape effective for producing from a plastic material by injection molding.

21. The ophthalmic device of claim 1, further comprising:
container stop means for seating the eyedrop container in the opening and preventing the outlet of the eyedrop container from extending further than a predetermined distance below the opening; and
wherein the means effective for reducing the opening when the lever arm members are squeezed together includes at least a void space extending in the longitudinal direction between the opening and-the lever arm members, and
wherein the ophthalmic device has a shape effective for producing from a plastic material by injection molding.

22. The ophthalmic device of claim 1, further comprising:
container stop means for seating the eyedrop container in the opening and preventing the outlet of the eyedrop container from extending further than a predetermined distance below the opening;
a sighting aperture for facilitating aligning the outlet of the eyedrop container directly over the recipient eye; and
wherein the means effective for reducing the opening when the lever arm members are squeezed together includes at least a void space extending in the longitudinal direction between the opening and the lever arm members; and
wherein the ophthalmic device has a shape effective for producing from a plastic material by injection molding.

23. An ophthalmic device for facilitating dispensing of an eyedrop from a resilient eyedrop container having a drop dispensing outlet, the ophthalmic device having a shape effective for producing from plastic material in a single injection molding step, the ophthalmic device comprising:
an unitary injection-moldable shaped body having
a front portion,
an opening for seating the eyedrop container with the outlet pointing down,
alignment means for resting on an user facial area and for facilitating maintaining the outlet of the eyedropper container in alignment with a recipient eye;
a first lever arm member rigidly connected to the front portion and extending in a longitudinal direction therefrom, and
a second lever arm member rigidly connected to the front portion and extending in the longitudinal direction therefrom, with distal ends of the lever arm members being spaced apart, the lever arm members having length effective for providing mechanical leverage for compressing of the eyedrop container seated in the opening and facilitating dispensing of an eyedrop.

24. The ophthalmic device of claim 23, wherein a ratio of a distance between a center of the opening and the distal ends of the lever arm members to a diameter of the opening is at least 1.0.

25. The ophthalmic device of claim 23, wherein a ratio of a distance between a center of the opening and the distal ends of the lever arm members to a diameter of the opening is at least about 1.5.

\* \* \* \* \*